United States Patent
Wenzel

(10) Patent No.: US 8,920,501 B2
(45) Date of Patent: Dec. 30, 2014

(54) IMPLANT SYSTEM HAVING AT LEAST THREE SUPPORT ELEMENTS

(75) Inventor: Rudolf Wenzel, Zuesch (DE)

(73) Assignee: Advance Medical Technologies, AG, Deggendorf (DE)

( * ) Notice: Subject to any disclaimer, the term of this patent is extended or adjusted under 35 U.S.C. 154(b) by 124 days.

(21) Appl. No.: 13/254,615

(22) PCT Filed: Mar. 4, 2010

(86) PCT No.: PCT/EP2010/052750
§ 371 (c)(1),
(2), (4) Date: Oct. 4, 2011

(87) PCT Pub. No.: WO2010/100222
PCT Pub. Date: Sep. 10, 2010

(65) Prior Publication Data
US 2012/0136443 A1   May 31, 2012

(30) Foreign Application Priority Data

Mar. 4, 2009 (DE) .......................... 10 2009 011 648

(51) Int. Cl.
*A61F 2/44* (2006.01)
*A61F 2/30* (2006.01)
*A61F 2/32* (2006.01)
*A61F 2/38* (2006.01)
*A61F 2/42* (2006.01)
*A61F 2/34* (2006.01)
*A61F 2/36* (2006.01)

(52) U.S. Cl.
CPC ............ *A61F 2/30767* (2013.01); *A61F 2/32* (2013.01); *A61F 2/38* (2013.01); *A61F 2/42* (2013.01); *A61F 2/44* (2013.01); *A61F 2/442* (2013.01); *A61F 2002/30733* (2013.01); *A61F 2002/30934* (2013.01); *A61F 2002/3496* (2013.01); *A61F 2002/3623* (2013.01); *A61F 2310/00023* (2013.01); *A61F 2310/00179* (2013.01); *A61F 2310/00389* (2013.01)
USPC ...................................... 623/17.14; 623/23.4

(58) Field of Classification Search
CPC ............ A61F 2002/30247; A61F 2002/30934; A61F 2002/30733; A61F 2310/00023; A61F 2310/00179
USPC .......... 623/17.11–17.16, 19.12, 20.22, 21.13, 623/21.16, 23.4, 22.15
See application file for complete search history.

(56) References Cited

U.S. PATENT DOCUMENTS 5,181,926 A    1/1993  Koch et al.
5,197,987 A *  3/1993  Koch et al. ................. 623/20.28
(Continued)

FOREIGN PATENT DOCUMENTS

DE    20320454 U1    10/2004
DE    60107818 T2    12/2005
(Continued)

OTHER PUBLICATIONS

International Search Report for PCT/EP2010/052750 English Translation attached to original, Both completed by the European Patent office on May 5, 2010, 6 Pages all together.

*Primary Examiner* — Ellen C Hammond
*Assistant Examiner* — Jacqueline Johanas

(57) ABSTRACT

An implant system that includes a concave spherical-segment-shaped socket part and a corresponding convex spherical-segment-shaped joint part is provided. The joint part rests in the socket part, wherein at least three support elements that describe a spherical triangle or a spherical polygon are arranged on the surface of the joint part or on the surface of the socket part.

20 Claims, 4 Drawing Sheets

(56) References Cited

U.S. PATENT DOCUMENTS

| | | | | |
|---|---|---|---|---|
| 5,425,773 | A * | 6/1995 | Boyd et al. | 623/17.15 |
| 5,549,700 | A * | 8/1996 | Graham et al. | 623/22.14 |
| 6,517,580 | B1 | 2/2003 | Ramadan et al. | |
| 7,077,867 | B1 * | 7/2006 | Pope et al. | 623/20.14 |
| 7,402,177 | B2 * | 7/2008 | Jones et al. | 623/22.39 |
| 7,442,211 | B2 * | 10/2008 | de Villiers et al. | 623/17.14 |
| 7,473,276 | B2 * | 1/2009 | Aebi et al. | 623/17.15 |
| 7,494,507 | B2 * | 2/2009 | Dixon et al. | 623/17.14 |
| 7,665,898 | B2 * | 2/2010 | Pope et al. | 384/492 |
| 7,758,653 | B2 * | 7/2010 | Steinberg | 623/23.5 |
| 8,002,842 | B2 * | 8/2011 | Ronk | 623/22.24 |
| 8,097,036 | B2 * | 1/2012 | Cordaro et al. | 623/17.15 |
| 8,163,023 | B2 * | 4/2012 | Nguyen et al. | 623/17.14 |
| 8,241,366 | B2 * | 8/2012 | Roche et al. | 623/19.13 |
| 8,679,181 | B2 * | 3/2014 | Lechmann et al. | 623/17.14 |
| 2002/0133234 | A1 * | 9/2002 | Sotereanos | 623/23.26 |
| 2003/0114935 | A1 * | 6/2003 | Chan et al. | 623/22.21 |
| 2003/0208273 | A1 * | 11/2003 | Eisermann et al. | 623/17.14 |
| 2004/0034433 | A1 * | 2/2004 | Chan et al. | 623/23.39 |
| 2004/0111159 | A1 * | 6/2004 | Pope et al. | 623/17.14 |
| 2005/0043802 | A1 * | 2/2005 | Eisermann et al. | 623/17.16 |
| 2005/0055098 | A1 * | 3/2005 | Zdeblick et al. | 623/17.11 |
| 2005/0085915 | A1 * | 4/2005 | Steinberg | 623/17.16 |
| 2005/0216086 | A1 * | 9/2005 | Marik et al. | 623/17.15 |
| 2005/0216092 | A1 * | 9/2005 | Marik et al. | 623/23.39 |
| 2006/0190079 | A1 * | 8/2006 | Istephanous et al. | 623/17.11 |
| 2006/0212122 | A1 * | 9/2006 | Perera | 623/17.14 |
| 2006/0235526 | A1 * | 10/2006 | Lemaire | 623/17.14 |
| 2006/0247777 | A1 | 11/2006 | Stamp | |
| 2007/0032877 | A1 * | 2/2007 | Whiteside | 623/22.15 |
| 2007/0106391 | A1 * | 5/2007 | Ronk | 623/22.21 |
| 2007/0168037 | A1 * | 7/2007 | Posnick | 623/17.14 |
| 2007/0179614 | A1 * | 8/2007 | Heinz et al. | 623/17.12 |
| 2008/0114461 | A1 * | 5/2008 | Collazo | 623/19.14 |
| 2008/0195212 | A1 * | 8/2008 | Nguyen et al. | 623/17.16 |
| 2008/0215158 | A1 * | 9/2008 | Pope et al. | 623/22.16 |
| 2009/0192624 | A1 * | 7/2009 | Collazo | 623/19.14 |

FOREIGN PATENT DOCUMENTS

| | | | |
|---|---|---|---|
| EP | 0497079 B1 | 5/1996 | |
| EP | 1321113 A2 | 6/2003 | |
| FR | 1538101 A | 8/1968 | |
| FR | 2134170 A1 | 12/1972 | |
| GB | 1527498 * | 10/1978 | A61F 2/32 |

* cited by examiner

IMPLANT SYSTEM HAVING AT LEAST THREE SUPPORT ELEMENTS

CROSS-REFERENCE TO RELATED APPLICATION

This application is the U.S. national phase of PCT Appln. No. PCT/EP2010/052750 filed Mar. 4, 2010 which claims priority to German application DE 10 2009 011 648.6 filed Mar. 4, 2009, the disclosure of which is incorporated in its entirety by reference herein.

The invention relates to an implant system comprising a concave spherical-segment-shaped socket part and a corresponding convex spherical-segment-shaped joint part, wherein the joint part rests in the socket part, in accordance with the combination of features as per claim 1.

Many possible material combinations are known in the field of prostheses. The origin of implant technology can be seen in the use of implant-grade steel, a material that is still used even today. In recent times, however, attempts have also been made to produce implants that consist, for example, of a combination of metal (e.g. implant-grade steel or titanium) and of ceramic.

By way of example, reference is made here to German Utility Model DE 203 20 454 U1. The latter document discloses an arrangement of components for a prosthesis, in particular for an intervertebral disk prosthesis for the cervical spine, which arrangement comprises two basic components with attached slide surfaces. The basic components preferably consist of polyether ether ketone and the slide surfaces, for example, of a Co—Cr alloy. Since polyether ether ketone has a modulus of elasticity similar to that of cortical bone, this material is particularly suitable, in view of its good elasticity features, for the connection surfaces between the implantable prosthesis and the exposed bone. In order to be able to achieve fusion of the bone onto the PEEK material, however, the material must undergo special treatment. The Co—Cr alloy used in the slide surfaces was employed because of the good slide properties and, at the same time, because of the low abrasion of the material.

DE 601 07 818 T2 uses a further combination of materials. This intervertebral disk prosthesis for the cervical spine consists primarily of a first plate and second plate, which plates are designed to be secured to adjacent cervical vertebrae. Moreover, a spherical joint is provided, which is arranged between the two plates lying secured one above the other, and the spherical joint consists of a spherical cap that cooperates with a spherical cup. The plates can advantageously be made of titanium, and the contact surfaces with the vertebral plates of the vertebrae are coated, for example, with hydroxyapatite or titanium with surface action in order to improve the anchoring between the prosthesis and the adjacent bones. The spherical joint can in turn have another material combination. The spherical cup can be made, for example, of zirconium oxide, and the corresponding spherical cap of aluminum oxide.

In prostheses, therefore, material combinations are used in order to ensure that, depending on the purpose of the individual component, the best suited material can be used. However, this often entails higher production costs and longer production times.

In order to keep costs and time to a minimum, attempts have also been made to produce prostheses of the abovementioned type from only one material, e.g. ceramic. This material is impressive especially because of its tissue compatibility and its property of not emitting substances into the environment, as is the case, for example, with metal implants (e.g. CoCr). This can trigger unpleasant reactions in sensitive individuals. Ceramic implants therefore have the advantage that they can also be used in persons who are sensitive to and have a reaction to metal.

However, ceramic has a crucial disadvantage. Prostheses that are designed as or contain a spherical joint, for example, cannot be economically produced such that the spherical cup and the spherical cap rest on each other across their entire surface without play. (Nor can this be achieved in metal implants). In the final analysis, this play condemns every spherical joint to have either a punctiform bearing or an annular bearing. In the case of a ceramic material, however, punctiform bearings of this kind sometimes have the effect that tensile forces result in early wear of the prosthesis and cause the prosthesis to break or move out of place.

Prostheses of this kind have to be removed again in an operation and replaced by a new implant system, and this operation entails further pain and inconvenience for the patient.

Therefore, in light of the above, the object of the present invention is to make available an implant system which permits an ideal distribution of force within an implant system and permits an improved useful life of the implant system.

The object is achieved by an implant system comprising a concave spherical-segment-shaped socket part and a corresponding convex spherical-segment-shaped joint part, wherein the joint part rests in the socket part, in accordance with the combination of features as per claim 1, while the dependent claims set forth at least expedient embodiments and developments.

According to the invention, at least three support elements that describe a spherical triangle or a spherical polygon are arranged on the surface of the joint part or on the surface of the socket part.

The described spherical-segment-shaped socket and joint parts can, on the one hand, be components of a hip joint, knee joint, elbow joint, ankle joint or wrist joint. On the other hand, the spherical-segment-shaped elements can be parts of an implant system for intervertebral disk prostheses in the cervical spine.

The advantage of the support elements on the surface of the socket part or joint part is, on the one hand, that the entire load acting on the implant system can be distributed to at least three points, instead of the customary one point. On the other hand, when at least three support elements are present within the socket part, the joint part can have no translation within the production-standard play.

The three support elements are arranged on the surface of the joint part or socket part, on the convex or concave curvature thereof, in such a way that they define a spherical triangle (in the case of three support elements) or a spherical polygon (in the case of more than three support elements). This means that at no time do all the support elements lie on an arc of a circle.

In a particularly preferred illustrative embodiment, the support elements are arranged spherically at 120° about a central point of the spherical-segment-shaped joint part or socket part. These angle details are not subject to any tolerance (the angle details do not have to be complied with for technical reasons), since the at least three support elements present always rest on the surface of the socket part or of the joint part.

In the arrangement of more than three support elements, it is advantageous to arrange these in such a way that the individual elements are arranged spherically at the same angle about a central point of the joint part or socket part.

According to the invention, the support elements are designed as punctiform elevations on the surface of the spherical-segment-shaped joint part or of the spherical-segment-shaped socket part. On the for example curved surface of the joint part or of the socket part, individual elements are thus arranged which form the punctiform elevations of the support elements. For example, the elements can be cap-shaped or pyramid-shaped configurations which, because they rest on the surface of the joint part or of the socket part (depending on which part the support elements are mounted), represent support elements in the form of punctiform elevations.

It will be noted at this juncture that the curved surfaces of the joint part and socket part described in the embodiments represent only one example of the shape of the individual parts of the implant system. Thus, for example, the surfaces can also be flat or provided with inclines.

In another embodiment, the support elements are designed as planar elevations in relation to the surface of the spherical-segment-shaped joint part or socket part. In this case, elements in the form of small prisms or cylinders, for example, are mounted on the surface of the joint part or socket part and, because they rest on the surface of the joint part or socket part, they form a support element in the form of a planar elevation.

It is also conceivable that the support elements are not only formed on a uniformly curved socket part or joint part, and instead the respective surfaces of the socket part or joint part in the area of the support elements form a plane or recess or have a smaller radius of curvature in relation to the overall surface of the joint part or socket part.

By means of such configurations, it is possible to form the implant system as a structure that is free of tensile forces.

The whole of the described implant system is preferably made of ceramic material. However, it is also conceivable for the described arrangement of the support elements to be formed in a metal or plastic implant. Titanium may be mentioned as an example of a metal material and PEEK as an example of a plastic material. Material combinations are also conceivable in which the joint part can be made of titanium, for example, and the joint part inter alia of PEEK.

The support elements are in turn preferably made of ceramic. In an illustrative embodiment, ceramic support elements of this kind are pressed into the titanium or PEEK plates of the joint part or socket part.

The support elements are expediently less rough than the rest of the surface of the socket part or joint part, such that the support elements are smoother than the rest of the surface of the respective component of the implant system.

In order to achieve a smooth surface of this kind, the support elements are surface-treated. The elements are preferably polished, because this is a relatively simple production step. This has the advantage that it is not necessary to polish the entire part on which the support elements are arranged, and instead only the support elements that come into contact with the corresponding implant system part are worked.

It is also possible that the support elements are coated with another material, such that, for example, a smoother or more resistant surface can be provided by the material coating.

It is also conceivable to coat the surfaces of the implant system directed toward the bone. Thus, for example, a coating with titanium or special ceramics is possible in order, on the one hand, to alter the mechanical properties of the implant system and, on the other hand, to ensure improved fusion of the bone onto the implant system.

The described implant system with the support elements according to the invention can preferably be used in connection with prostheses in the spinal column area. A use as an intervertebral disk prosthesis is thus conceivable.

However, it is also possible to use the described construction in the production of hip implants. In such a case, the described socket part represents the acetabulum and the joint part represents the articulating bone located on the femur.

The invention is explained in more detail below on the basis of a number of illustrative embodiments and with reference to the figures, in which.

Figure 1:
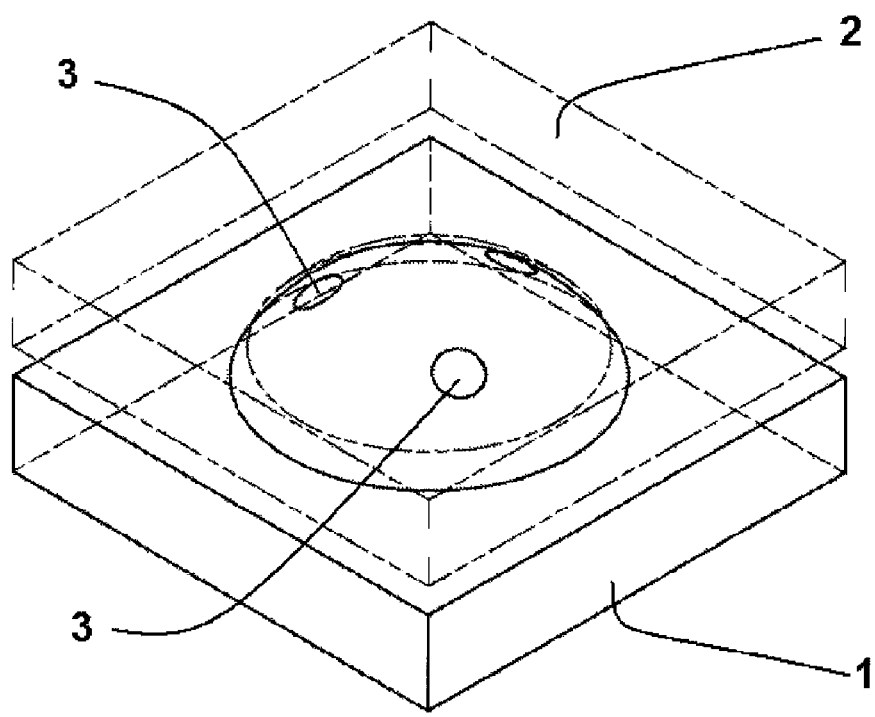
FIG. 1 shows a view of an implant system according to the invention with support elements as punctiform elevations.

As is shown in FIG. 1, the implant system according to the invention consists of a joint part 1 and the socket part 2. It will be noted that the joint part 2 is in the form of a convex spherical-segment-shaped element and the socket part 2 is in the form of a corresponding concave spherical-segment-shaped element.

In the embodiment in FIG. 1, three support elements 3 are located on the joint part 1 and are arranged spherically at 120° to one another about the central point of the curved joint part. It is also evident that the support elements 3 describe a spherical triangle.

At imaginary connection lines, the support elements 3 enclose a spherical triangle. However, if more than 3 support points are used, these enclose a spherical polygon. The advantage of constructing an implant system with three support elements is that the support elements always rest in the spherical segment independently of the distances of the support elements from one another and independently of tolerances being maintained.

Figure 2:
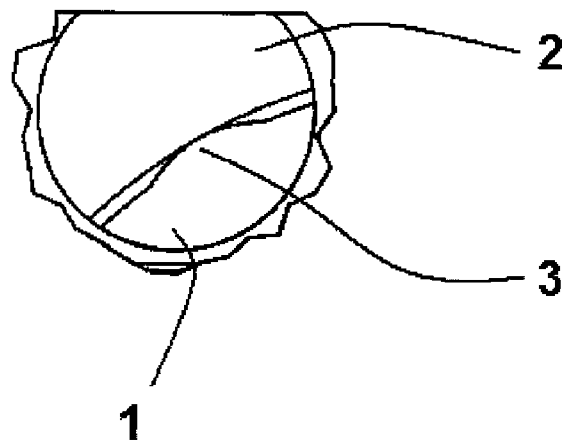
FIG. 2 shows a view of the support element resting on the socket part.

The interaction between the support elements 3 and the socket part 2 in contact therewith is shown in FIG. 2. The detail shows a support element 3 that is arranged on the joint part 1 and that touches the concave surface of the socket part 2. The design of the support element 3 as a spherical segment results in a punctiform contact.

Figure 3:
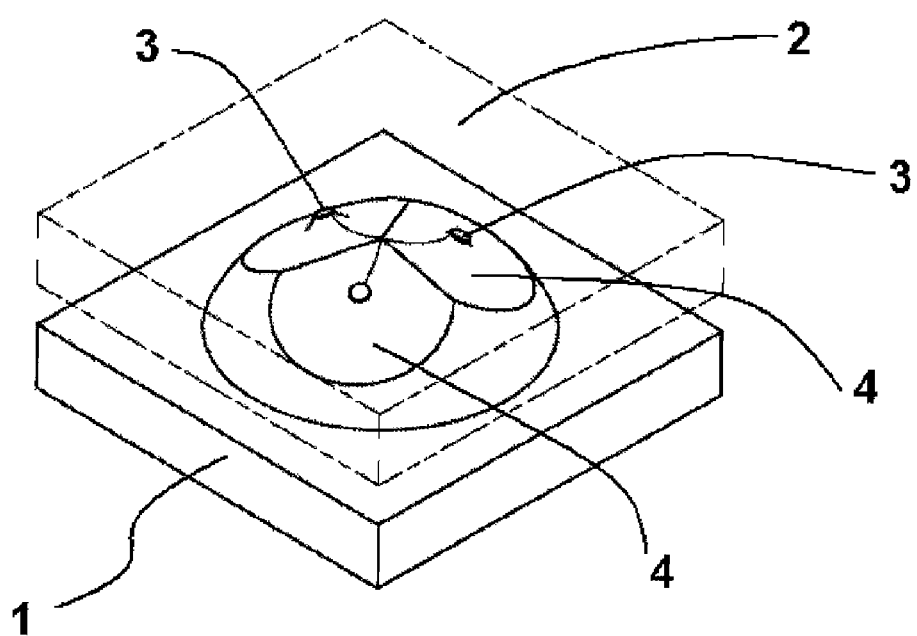
FIG. 3 shows a view of an implant system according to the invention with recesses formed in the joint part and with support elements in the form of planar elevations.

FIG. 3 shows another illustrative embodiment of the implant system according to the invention. In this case too, the three support elements 3 are located on the surface of the joint part 1, but on a recess 4 instead of directly on a uniformly convex surface. This recess 4 has a concave curvature, at the center of which the support elements 3 are each mounted.

The concave curvatures serve to make available a construction that is free from tensile force, which is particularly important in the production of a ceramic implant system.

Figure 4:
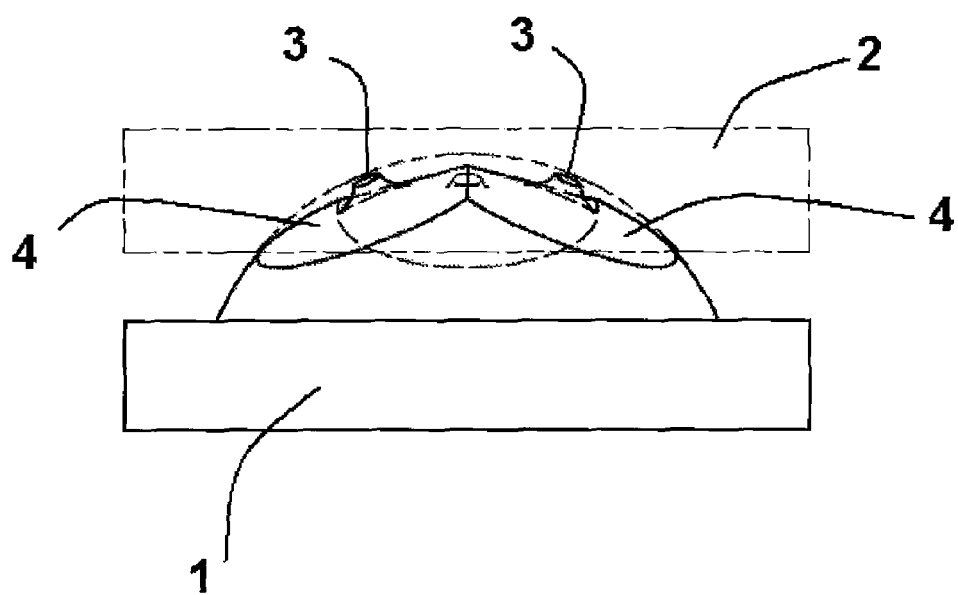
FIG. 4 shows another view of an implant system according to the invention with recesses formed in the joint part and with support elements in the form of planar elevations.

It should also be noted in the embodiment according to FIGS. 3 and 4 that the support elements 3 are in this case in the form of a planar elevation. That is to say the support elements 3 have the basic shape of a truncated cone which, as is known, is flattened on its top. In an assembled implant system, this flattening is in full contact with the surface of the socket part 2.

LIST OF REFERENCE SIGNS 1 joint part
2 socket part
3 support element
4 recess

The invention claimed is:

1. An implant system comprising:
   a concave spherical-segment-shaped socket part; and
   a corresponding convex spherical-segment-shaped joint part, wherein the joint part rests in the socket part, a convex surface of the joint part comprising a plurality of recesses, wherein a support element extends from each of the recesses such that the support elements describe a spherical triangle, at least two of the recesses having a common boundary, the support elements being arranged spherically at 120° about a central point of the spherical-segment-shaped joint part, wherein the joint part comprises titanium or PEEK and the support elements comprise ceramic.

2. The implant system as claimed in claim 1, wherein the support elements are designed as planar elevations that engage a concave surface of the socket part to space the convex surface apart from the concave surface.

3. The implant system as claimed in claim 1, wherein the joint part comprises titanium and the recesses each extend into the titanium.

4. The implant system as claimed in claim 1, wherein the joint part comprises PEEK and the recesses each extend into the PEEK.

5. The implant system as claimed in claim 1, wherein the support elements are cylindrical.

6. The implant system as claimed in claim 1, wherein the support elements are less rough than the surface of the joint part.

7. The implant system as claimed in claim 1, wherein the support elements are surface-treated.

8. The implant system as claimed in claim 1, wherein the support elements are polished.

9. The implant system as claimed in claim 1, wherein the support elements are coated with another material.

10. The implant system as claimed in claim 1, wherein sides of the implant system configured to be directed toward bone are coated.

11. The implant system as claimed in claim 10, wherein the coating is titanium or ceramic.

12. The implant system as claimed in claim 1, wherein the support elements are each centrally positioned in a respective one of the recesses.

13. The implant system as claimed in claim 1, wherein the recesses each have a maximum diameter that is greater than that of each of the support elements such that each of the support elements is spaced apart from edges of a respective one of the recesses.

14. The use of an implant system as claimed in claim 1 in connection with prostheses in the spinal column area.

15. The use of an implant system as claimed in claim 1 in connection with a hip joint.

16. An implant system comprising:
    a first plate comprising a planar first surface and a concave spherical-segment-shaped socket part opposite the first surface;
    and a second plate comprising a planar second surface and a convex spherical-segment-shaped joint part opposite the second surface, wherein the joint part rests in the socket part such that a concave surface of the socket part faces a convex surface of the joint part, the convex surface comprising three recesses that intersect at a central point of the joint part, wherein a support element extends from each of the recesses such that the support elements describe a spherical triangle, the support elements being arranged spherically at 120° about the central point,
    wherein the joint part comprises titanium, the support elements comprise a ceramic material and the recesses extend into the titanium.

17. The implant system as claimed in claim 16, wherein planar side surfaces of the second plate are each perpendicular to an adjacent one of the side surfaces of the second plate.

18. An implant system comprising:
    a concave spherical-segment-shaped socket part; and
    a corresponding convex spherical-segment-shaped joint part that rests in the socket part such that a concave surface of the socket part faces a convex surface of the joint part, the convex surface comprising a plurality of concave recesses that abut one another, each of the recesses comprising a ceramic support element extending therefrom that engages the concave surface to space the convex surface apart from the concave surface,
    wherein the support elements describe a spherical triangle extending from the joint part, the support elements being arranged spherically at 120° about a central point of the joint part.

19. The implant system as claimed in claim 18, wherein the plurality of recesses comprises three recesses, each of the recesses including a single one of the support elements extending therefrom.

20. The implant system as claimed in claim 18, wherein the support elements each have a cylindrical configuration such that a planar end surface of each of the support elements engages the concave surface.

* * * * *